(12) United States Patent
Kurata et al.

(10) Patent No.: US 9,790,461 B2
(45) Date of Patent: Oct. 17, 2017

(54) CULTURE METHOD AND CULTURE SYSTEM FOR MICROALGAE

(71) Applicants: DENSO CORPORATION, Kariya, Aichi-pref. (JP); Kyoto University, Kyoto-shi, Kyoto-pref. (JP); Chuo University, Hachioji-shi, Tokyo (JP)

(72) Inventors: Minoru Kurata, Nagoya (JP); Hiroaki Fukuda, Obu (JP); Norihide Kurano, Nagoya (JP); Hideaki Miyashita, Kyoto (JP); Shigeaki Harayama, Tokyo (JP)

(73) Assignees: DENSO CORPORATION, Kariya, Aichi-pref. (JP); Kyoto University, Kyoto-shi, Koyoto-Pref. (JP); Chuo University, Hachioji-shi, Tokyo (JP)

( * ) Notice: Subject to any disclaimer, the term of this patent is extended or adjusted under 35 U.S.C. 154(b) by 0 days.

(21) Appl. No.: 14/651,164

(22) PCT Filed: Dec. 4, 2013

(86) PCT No.: PCT/JP2013/007118
§ 371 (c)(1),
(2) Date: Jun. 10, 2015

(87) PCT Pub. No.: WO2014/091718
PCT Pub. Date: Jun. 19, 2014

(65) Prior Publication Data
US 2015/0337255 A1 Nov. 26, 2015

(30) Foreign Application Priority Data
Dec. 14, 2012 (JP) ................................. 2012-273633

(51) Int. Cl.
C12M 1/00 (2006.01)
C12M 1/34 (2006.01)
C12N 1/12 (2006.01)
C12P 7/64 (2006.01)

(52) U.S. Cl.
CPC ............ *C12M 41/26* (2013.01); *C12M 21/02* (2013.01); *C12M 23/18* (2013.01); *C12M 41/34* (2013.01); *C12M 41/36* (2013.01); *C12N 1/12* (2013.01); *C12P 7/64* (2013.01)

(58) Field of Classification Search
CPC ......... Y02E 50/13; Y02E 50/17; Y02E 50/10; Y02E 50/343; C12P 7/6463; C12P 7/16; C12P 7/64; C12P 7/6445; C12P 7/649; C12P 7/06; C12P 7/065; C12P 39/00; C12P 7/46; C12P 3/00; C12P 5/023; C12P 7/08; C12P 5/02
See application file for complete search history.

(56) References Cited

U.S. PATENT DOCUMENTS

| 9,260,685 B2 * | 2/2016 | Herzog ................. C12M 21/02 |
| 2011/0020914 A1 * | 1/2011 | Abou-Nemeh .......... C12N 1/12 435/257.4 |
| 2011/0306101 A1 * | 12/2011 | De Crecy ............. C12P 7/6409 435/134 |

FOREIGN PATENT DOCUMENTS

| JP | H05284962 A | 11/1993 |
| JP | H05304945 A | 11/1993 |
| JP | H07059557 A | 3/1995 |
| JP | H07238488 A | 9/1995 |
| JP | H07289239 A | 11/1995 |
| JP | H08009963 A | 1/1996 |
| JP | H08056648 A | 3/1996 |
| JP | H09227602 A | 9/1997 |
| JP | H10248553 A | 9/1998 |

OTHER PUBLICATIONS

Mattson et al, Cornell University, "Nitrogen: All Forms Are Not Equal", pp. 1-5, Jun. 2009.*
International Search Report and Written Opinion (in Japanese with English Translation) for PCT/JP2013/007118, mailed Feb. 10, 2014; ISA/JP.
AquaFUELS-D1.4 Rev Nov. 7-30, 2010 PP28.36.
Co-hosted by Agriculture, Forestry and Fisheries Research Council & Research and Development Initiative Chuo University, International Symposium on Algel Biofuels, Nov. 17, 2011 (Nov. 17, 2011), all pages, reference URL <http://www.bio.chuo-u.ac.jp/harayama/u>.
Hiroaki Fukuda et al., "Biofuel Production from a Green Alga Pseudochoricystis ellipsoidea", Journal of The Japan Institute of Energy, Nov. 20, 2012 (Nov. 20, 2012), vol. 91, No. 11, pp. 1166 to 1171.
Wang H., et al., The contamination and control of biological pollutants in mass cultivation of microalgae, Bioresour. Technol., Nov. 7, 2012, vol. 128, p. 745-750, Epub.
Garbayo, Ines et al., Identification and Physiological Aspects of a Novel Carotenoid-Enriched, Metal-Resistant Microalga Isolated from an Acidic River in Huelva (Spain), J. Phycol, vol. 48, No. 3, pp. 607-614, Jun. 2012.
Carlos Casal et al., "Enhanced Productivity of a Lutein-Enriched Novel Acidophile Microalga Grown on Urea," Marine Drugs, 2011, vol. 9, pp. 29-42.

* cited by examiner

*Primary Examiner* — Debbie K Ware
(74) *Attorney, Agent, or Firm* — Harness, Dickey & Pierce, P.L.C.

(57) ABSTRACT

A culture method for microalgae that cultures unicellular green microalgae belonging to the genus *Coccomyxa* and groups of organisms closely related thereto, or the Watanabea clade, in an open outdoor culture system using broth having a pH of 4 or lower. A culture method for microalgae that cultures microalgae of the genus *Coccomyxa* and groups of organisms closely related thereto, or *Pseudococcomyxa*, in an open outdoor culture system using broth having a pH of 4 or lower containing ammonia nitrogen.

11 Claims, 4 Drawing Sheets

|  | NITROGEN CONTENT (WEIGHT %) | OIL AND FAT CONTENT (WEIGHT %) |
|---|---|---|
| 1ST EMBODIMENT | 3.1 | 22.4 |
| 2ND EMBODIMENT | 2.7 | 20.9 |
| 3RD EMBODIMENT | 2.7 | — |

FIG. 5

|  | OIL AND FAT CONTENT (WEIGHT %) |
|---|---|
| SECOND | 24.2 |
| THIRD | 24.8 |

CULTURE METHOD AND CULTURE SYSTEM FOR MICROALGAE

CROSS REFERENCE TO RELATED APPLICATIONS

This application is a U.S. National Phase Application under 35 U.S.C. 371 of International Application No. PCT/JP2013/007118 filed on Dec. 4, 2013 and published in Japanese as WO 2014/091718 A1 on Jun. 19, 2014. This application is based on and claims the benefit of priority from Japanese Patent Application No. 2012-273633 filed on Dec. 14, 2012. The entire disclosures of all of the above applications are incorporated herein by reference.

TECHNICAL FIELD

The present disclosure relates to a culture method and a culture system for microalgae.

BACKGROUND ART

Recently, usage and application of useful material such as oil and fat and saccharide produced by microalgae are attracted attention. To improve productivity of useful material, microalgae is required to be cultured effectively. Conventionally, a culturing method for microalgae mainly uses culture liquid which is neutral or alkaline (referring to non-patent document 1).

PRIOR ART DOCUMENT

Patent Document

Non-patent document 1: AquaFUELs-D1.4 Rev7-30 Nov. 2010 Page 28-36

SUMMARY OF THE INVENTION

The present disclosure has been made in view of the above, and aims to provide a culture method and a culture system for microalgae under an outdoor open system.

A culture method for microalgae according to a first aspect of the present disclosure uses culture liquid whose pH is equal to or less than 4 and cultures microalgae of the genus *Coccomyxa*, the closely related group of the genus *Coccomyxa*, or a green unicellular algae belonging to the Watanabea clade in an outdoor open culture system. According to the culture method, since the pH of the culture liquid is equal to or less than 4, it may be possible to inhibit proliferation of different microalgae and protist. Since bicarbonate ion is not generated even when CO2 is introduced in the culture liquid, it may be possible to prevent variation of the pH of the culture liquid.

A culture method for microalgae according to a second aspect of the present disclosure uses culture liquid including ammonia nitrogen and cultures microalgae of the genus *Coccomyxa*, the closely related group of the genus *Coccomyxa*, and the genus *Pseudococcomyxa* in an outdoor open culture system. The pH of the culture liquid is equal to or less than 4. According to the culture method, since the pH of the culture liquid is equal to or less than 4, it may be possible to inhibit proliferation of different microalgae and protist. Especially, since the culture liquid includes ammonia nitrogen (for example, urea), it may be possible to inhibit proliferation of different microalgae and protist. Since bicarbonate ion is not generated even when CO2 is introduced in the culture liquid, it may be possible to prevent variation of the pH of the culture liquid.

BRIEF DESCRIPTION OF THE DRAWINGS

The above-described and other objects, features, and advantages of the present disclosure will become more obvious through the specific description below with reference to the accompanying figures. In the drawings:

FIG. 5 is a diagram illustrating oil-and-fat content in an algae body after the second culture and after the third culture.

PREFERRED EMBODIMENTS FOR CARRYING OUT THE INVENTION

Figure 1:
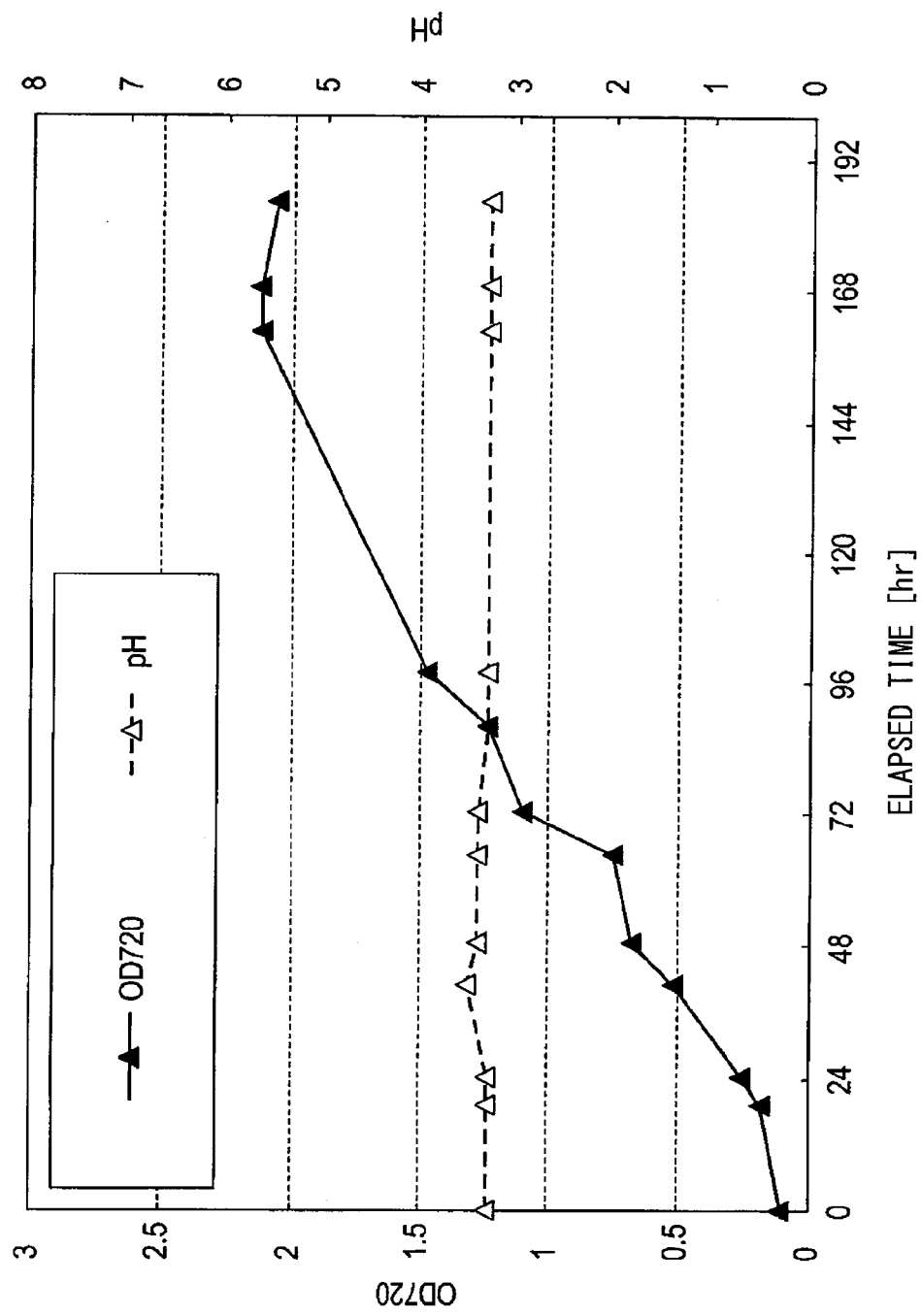
FIG. 1 is a graph illustrating a transition of algae body concentration and pH in a first embodiment.

When culture liquid is neutral liquid or alkaline liquid, microalgae (hereinafter, referred to as a different microalgae) other than microalgae to be cultured and protist that preys on microalgae may propagate. When microalga is cultured, CO2 may be introduced into culture liquid continuously. However, when the culture liquid is neutral liquid or alkaline liquid, bicarbonate ion may be generated from CO2 and the pH of the culture liquid may be changed. In this case, an introduction of a pH adjuster to the culture liquid may be required and salt concentration in the culture liquid may increase.

The embodiment in the present disclosure will be explained. Microalgae to be cultured in a culture method in the present disclosure corresponds to the genus *Coccomyxa*, the closely related group of the genus *Coccomyxa*, the genus *Pseudococcomyxa*, or the green unicellular algae belonging to the Watanabea clade. Especially, the microalgae to be cultured in the culture method in the present disclosure corresponds to a microalgae that is screened by a predetermined isolation condition (for example, the pH is equal to 3 and temperature is 15-35 degrees Celsius) from a sample sampled in a hot spring gushing environment or the like (that is, the microalgae to be cultured corresponds to microalgae enabling to grow in the above isolation condition).

The microalgae selected by the above screening condition from a sample obtained in a hot spring gushing environment or the like corresponds to, for example, the Pseudochoricystis ellipsoidea N1 strain (MBIC11204: closely related to the genus *Pseudococcomyxa*), the Pseudochoricystis ellipsoidea Obi strain (MBIC11220: closely related to the genus *Pseudococcomyxa*), *Coccomyxa* simplex (UTEX274: the genus *Coccomyxa*), and *Coccomyxa chodatii* (UTEXB266: the genus *Coccomyxa*).

A microalgae of the genus *Coccomyxa*, the closely related group of the genus *Coccomyxa*, the genus *Pseudococcomyxa*, or green unicellular algae belonging to the Watanabea clade may be selected from the sample obtained in a hot spring gushing environment or the like according to the above screening condition, and may be used in the culture method in the present disclosure. Incidentally, it may be possible to confirm that the microalgae corresponds the genus *Coccomyxa*, the closely related group of the genus *Coccomyxa*, the genus *Pseudococcomyxa*, or the green unicellular algae belonging to the Watanabea clade with a homology of DNA, and an identity in the 18S rRNA is equal to or more than 97%. The identity in the 18S rRNA is confirmed by using a well-known DNA data base.

A culture liquid in the culture method in the present disclosure may be culture liquid having a well-known composition. The pH of the culture liquid is equal to or less than 4, and preferably, corresponds to pH 3-4. In the culture method in the present disclosure, for example, the culture liquid may be continuously introduced with CO2 (CO2 containing gas). In this case, culture speed of the microalgae keeps in a high level. Incidentally, since the pH of the culture liquid is equal to or less than 4, bicarbonate may be generated hardly and the pH of the culture liquid may be changed hardly.

In the culture method in the present disclosure, ammonia nitrogen may be included in the culture liquid. In this case, the propagation of the different microalgae and the protist may be hardly generated furthermore. The ammonia nitrogen is not limited especially. The ammonia nitrogen may be urea, for example.

In the culture method in the present disclosure, for example, all or a part of the microalgae may be recovered from the culture liquid used in a culture of the microalgae, and the microalgae may be newly cultured by adding a deficient medium component. In this case, since it may be possible to reuse the culture liquid, it may be possible to reduce a culture cost of the microalgae.

The culture method in the present disclosure uses, for example, a culture system including a detection means and a control means. The detection means detects one or more parameters selected from a parameter group including pH, CO2 concentration, and algae body concentration in a culture liquid. The control means controls the parameter within a predetermined range. According to the culture system, it may be easy to maintain the parameter within a suitable range. Incidentally, the detection means corresponds to a detector. The control means corresponds to a controller.

When the parameter includes pH, the culture system detects the pH by the detection means, and maintains the pH within a range of 4 or less (preferably, pH 3 to 4) with the control means. When the parameter includes CO2 concentration, the culture system detects the CO2 concentration with the detection means, and maintains the CO2 concentration within a predetermined range with the control means. The predetermined range corresponds to, for example, 7.45-74.5 mg/L.

The detection means corresponds to, for example, a sensor (for example, a pH measurement sensor, a CO2 concentration measurement sensor, and an algae concentration measurement sensor) capable of measuring the parameter. The control means corresponds to a means, for example, including an adjustment means (for example, a valve mechanism adjusting introducing amount of a pH adjuster to the culture liquid, a valve mechanism adjusting introducing amount of CO2 containing gas to the culture liquid, and a valve mechanism adjusting introducing amount of microalgae to the culture liquid) to adjust the parameter and a computer that controls the adjustment means according to a measurement result of the above sensor.

First Embodiment

An outdoor open culture system (500 L) stores the culture liquid having the following composition.
Ion exchange water: 500 kg
Ammonia nitrogen (Urea): 9.8 g
Phosphorus: 560 mg
Potassium: 560 mg
Calcium: 150 mg
Magnesium: 170 mg
Chelated metal salt: 85 mg
The pH of the culture liquid is adjusted to 3.5 with hydrochloric acid before inoculation of the microalgae. The pH of the culture liquid was not adjusted thereafter. Pseudochoricystis ellipsoidea N1 strain (MBIC11204), which is a closely related microalgae of the genus *Pseudococcomyxa*, is inoculated to the culture liquid to have 0.02 g/l.

Figures 3, 4:
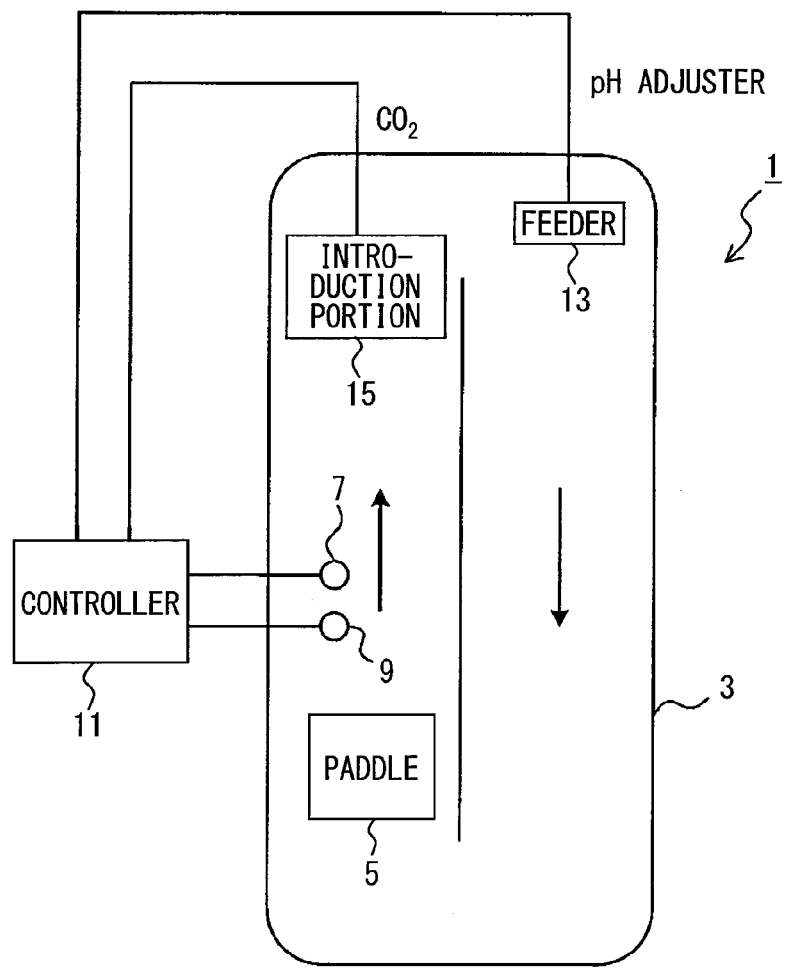
FIG. 3 is a diagram illustrating a configuration of a culture system 1.
FIG. 4 is a diagram illustrating nitrogen concentration and oil-and-fat content in an algae body after culture.

Insolation by the sun is used as a light source and gas including 1 volume % of CO2 is continuously ventilated to the culture liquid during the culture. The algae body concentration and the pH in the culture liquid are continuously measured during the culture. FIG. 1 illustrates the measurement result. In FIG. 1, OD720 illustrates the algae body concentration during culture and the pH illustrates the pH of the culture liquid. In addition, the nitrogen concentration and oil-and-fat content in the algae body after culture were measured. FIG. 4 illustrates the result.

As described in FIG. 1 and FIG. 4, the pH in the culture liquid was changed hardly during culture, and the growth of the microalgae was good. The growth of the different microalgae and the protist was not seen.

Second Embodiment

As the microalgae, instead of Pseudochoricystis ellipsoidea N1 strain (MBIC11204), which is a closely related microalgae of the genus *Pseudococcomyxa*, Pseudochoricystis ellipsoidea Obi strain (MBIC11220), which is a closely related microalgae of the genus *Pseudococcomyxa*, is used and the culture is performed in a manner similar to the first embodiment.

The nitrogen concentration and the oil-and-fat content in the algae body after culture were measured. FIG. 4 illustrates the result. As illustrated in FIG. 4, the growth of microalgae was good. During the culture, the pH in the culture liquid was changed hardly, and the growth of the different microalgae and the protist was not seen.

Third Embodiment

As the microalgae, instead of Pseudochoricystis ellipsoidea N1 strain (MBIC11204), *Coccomyxa simplex* (UTEX274) is used and the culture is performed in a manner similar to the first embodiment.

The nitrogen concentration and the oil-and-fat content in the algae body after culture were measured. FIG. 4 illustrates the result. As illustrated in FIG. 4, the growth of microalgae was good. During culture, the pH in the culture liquid was changed hardly, and the growth of the different microalgae and the protist was not seen.

Fourth Embodiment

As the microalgae, instead of Pseudochoricystis ellipsoidea N1 strain (MBIC11204), *Coccomyxa chodatii* (UTEXB266) is used and the culture is performed in a manner similar to the first embodiment.

When the nitrogen concentration and the oil-and-fat content in the algae body after culture were measured, it was supported that the growth of the microalgae is good. During culture, the pH in the culture liquid was changed hardly, and the growth of the different microalgae and the protist was not seen.

Fifth Embodiment

An outdoor open culture system (500 L) stores a culture liquid having the following composition.
Ion exchange water: 500 kg
Nitrate nitrogen (sodium nitrate): 27.3 g Phosphorus: 560 mg
Potassium: 560 mg
Calcium: 150 mg
Magnesium: 170 g
Chelated metal salt: 85 mg The pH of the culture liquid is adjusted to 3 with hydrochloric acid before inoculation of the microalgae. The pH of the culture liquid was not adjusted thereafter. The green unicellular algae belonging to the Watanabea clade is inoculated to the culture liquid to have 0.02 g/l. The microalgae corresponds to a microalgae screened in a condition that the pH is equal to 3 and temperature is 15-35 degrees Celsius from a sample sampled in a hot spring gushing environment or the like. It is confirmed that the microalgae corresponds to a green unicellular algae belonging to the Watanabea clade by the homology of DNA. The DNA sequences of the microalgae are illustrated in sequence IDs 4-6 in the sequence listings.

Insolation by the sun is used as a light source and gas including 1 volume % of carbon dioxide concentration is continuously ventilated to the culture liquid during culture. The pH in the culture liquid was changed hardly, and growth of the microalgae was good during culture. The growth of the different microalgae and the protist was not seen.

Sixth Embodiment

The microalgae same as the first embodiment is used and the culture is performed in a manner similar to the first embodiment. This is named as a first culture. The microalgae is recovered from the culture liquid after the first culture. In the culture liquid (which is the culture liquid substantially including no microalgae) after recovering the microalgae, a microalgae (the microalgae same as the first embodiment) is newly cultured in a manner similar to the first embodiment. This is named as a second culture. With respect to the medium composition of the culture liquid, the medium compositions identical with the first embodiment are added.

Subsequently, the microalgae is recovered from the culture liquid after the second culture. In the culture liquid (which is culture liquid substantially including no microalgae) after recovering the microalgae, a microalgae (the microalgae same as the first embodiment) is newly cultured in a manner similar to the first embodiment. This is named as a third culture. With respect to the medium composition of the culture liquid, the medium compositions identical with the first embodiment are added.

Figure 2:
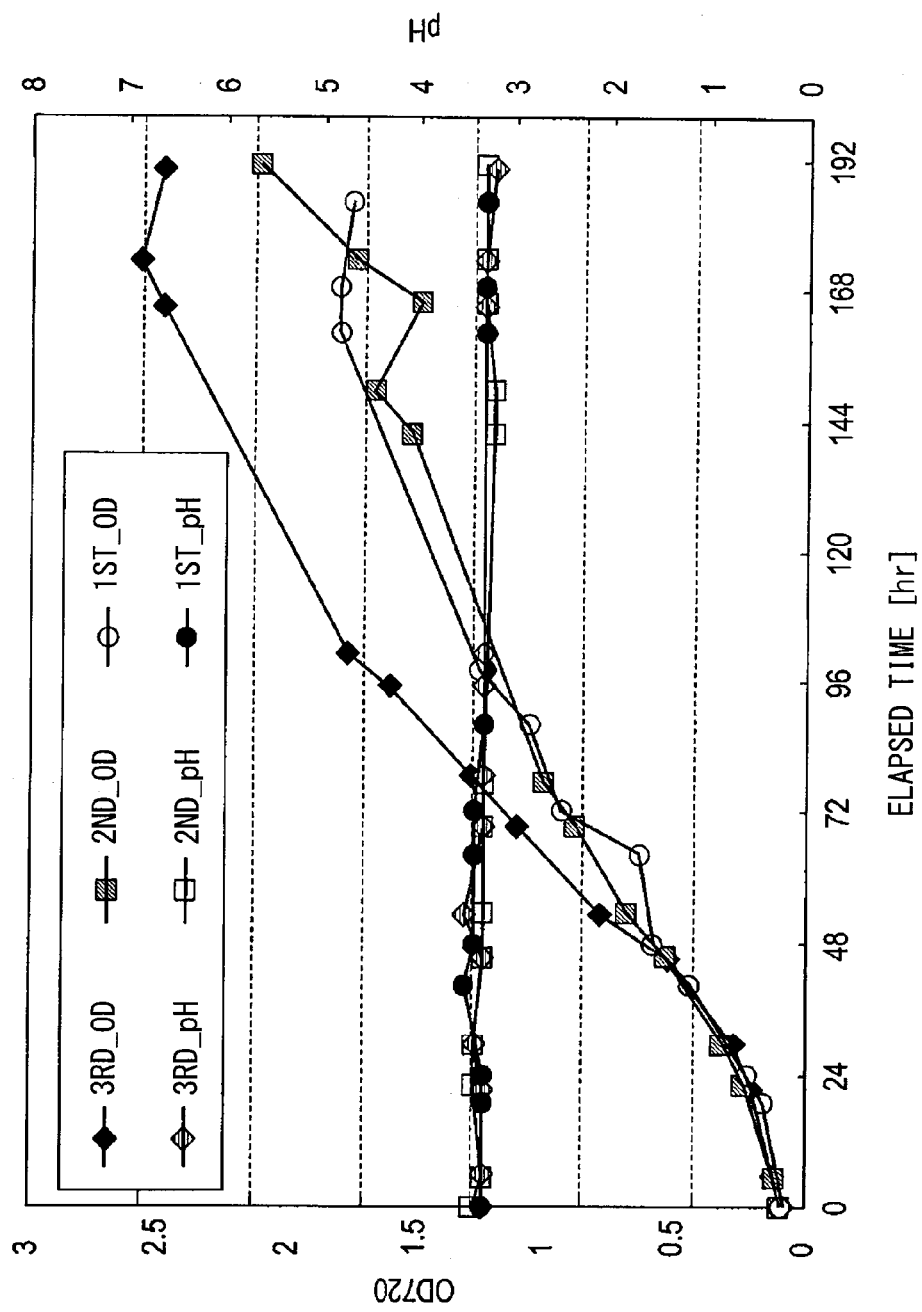
FIG. 2 is a graph illustrating a transition of algae body concentration and pH in a second embodiment.

FIG. 2 illustrates the algae body concentration (OD720) after the first culture, the pH after the first culture, the algae body concentration (OD720) after the second culture, the pH after the second culture, the algae body concentration (OD720) after the third culture, and the pH after the third culture. FIG. 5 illustrates the oil-and-fat content in the algae body after the second culture and after the third culture. Incidentally, in FIG. 2, the algae body concentration after the n-th (n=1, 2, 3) culture is described as an n-th_OD, and the pH after the n-th culture is described as an n-th_pH.

As described in FIG. 2 and FIG. 5, the growth of the microalgae was good and the pH was changed hardly in any of the first to third cultures.

Seventh Embodiment

With a mixture containing various microbes obtained from a hot spring, a culture is performed in a manner similar to the fifth embodiment. In this case, only microalgae of the genus *Coccomyxa*, the closely related group of the genus *Coccomyxa*, the genus *Pseudococcomyxa*, or the green unicellular algae belonging to the Watanabea clade is proliferated. The DNA sequences of microalgae of the genus *Coccomyxa*, the closely related group of the genus *Coccomyxa*, and the genus *Pseudococcomyxa* are described as sequence IDs 1-3 in the sequence listings. The DNA sequences of microalgae of a green unicellular algae belonging to the Watanabea clade are described as sequence IDs 4-6 in the sequence listings.

Eighth Embodiment

With a mixture containing various microbes obtained from a hot spring, a culture is performed in a manner similar to the first embodiment. In this case, only microalgae of the genus *Coccomyxa*, the closely related group of the genus *Coccomyxa*, and the genus *Pseudococcomyxa* is proliferated. The DNA sequences of the microalgae of the genus *Coccomyxa*, the closely related group of the genus *Coccomyxa*, and the genus *Pseudococcomyxa* are illustrated as sequence IDs 1-3 in the sequence listings.

Ninth Embodiment

FIG. 3 illustrates a configuration of a culture system 1. The culture system 1 includes a raceway-type culture tank 3, an agitation paddle 5 that agitates the culture liquid in the culture tank 3, a pH measurement sensor 7 that detects pH in the culture liquid, a CO2 concentration measurement sensor 9 that detects the CO2 concentration in the culture liquid, a controller 11 including a well-known computer, a pH adjuster feeder 13 that inputs pH adjuster to the culture liquid, and a CO2 gas introduction portion 15 that introduces CO2 containing gas to the culture liquid.

The pH adjuster feeder 13 has a well-known valve mechanism. The pH adjuster feeder 13 enables to adjust input amount of the pH adjuster to the culture liquid. The CO2 gas introduction portion 15 has a well-known valve mechanism. The CO2 gas introduction portion 15 enables to adjust introduction amount of the CO2 containing gas to the culture liquid.

The controller 11 obtains a measurement result of the pH measurement sensor 7. The controller 11 controls the pH adjuster feeder 13 to input the pH adjuster as necessary, so that the pH in the culture liquid is maintained within a range of pH 3-4.

The controller 11 obtains a measurement result of the CO2 concentration sensor 9. The controller 11 controls the CO2 gas introduction portion 15 to adjust introduction amount of the CO2 containing gas to the culture liquid, so that the CO2 concentration in the culture liquid is maintained within a range of 7.45-74.5 mg/L. Incidentally, the pH measurement sensor 7 and the CO2 concentration measurement sensor 9 correspond to one embodiment of a detection means. The controller 11, the pH adjuster feeder 13, and the CO2 gas introduction portion 15 correspond to one embodiment of a control portion.

The culture system 1 in the present embodiment may be applied to the culture of the microalgae in the first to sixth embodiments. When the culture system 1 in the present embodiment is used, it may be easy to maintain the pH and the CO2 concentration in the culture liquid within the suitable range.

The culture system 1 may include a sensor that measures the algae body concentration in the culture liquid and a means that adjusts the algae body concentration within a predetermined range according to the measurement result of the sensor. In this case, since the controller 11 adjusts the algae body concentration according to the measurement result of the algae body concentration, it may be possible to maintain the algae body concentration within a suitable range.

A culture method for microalgae according to a first aspect of the present disclosure uses culture liquid whose pH is equal to or less than 4 and cultures microalgae of the genus *Coccomyxa*, the closely related group of the genus *Coccomyxa*, or a green unicellular algae belonging to the Watanabea clade in an outdoor open culture system. According to the culture method, since the pH of the culture liquid is equal to or less than 4, it may be possible to inhibit proliferation of the different microalgae and the protist. Since bicarbonate ion is not generated even when CO2 is introduced into the culture liquid, it may be possible to prevent a variation of the pH in the culture liquid.

The culture method of the microalgae according to a second aspect of the present disclosure uses culture liquid containing ammonia nitrogen and cultures microalgae of the genus *Coccomyxa*, the closely related group of the genus *Coccomyxa*, and the genus *Pseudococcomyxa* in an outdoor open culture system. The pH of the culture liquid is equal to or less than 4. According to the culture method, since the pH of the culture liquid is equal to or less than 4, it may be possible to inhibit proliferation of the different microalgae and the protist. Especially, since the culture liquid includes ammonia nitrogen (for example, urea), it may be possible to inhibit proliferation of the different microalgae and protist. Since bicarbonate ion is not generated even when CO2 is introduced into the culture liquid, it may be possible to prevent a variation of the pH in the culture liquid.

Incidentally, the present disclosure is not limited to the present embodiment. It should be noted that the present disclosure may be realized in various modes within a scope of the present disclosure. For example, in the first to fourth, sixth, and eighth embodiments, instead of urea, a substantially similar effect will be obtained when different ammonia nitrogen is used.

As described above, a culture method and a culture system of a microalgae according to the present disclosure are exemplified. However, a mode and a configuration according to the present disclosure are not limited to each embodiment and each configuration. The embodiments and the configurations obtained by appropriately combining the respective technical elements disclosed in the different embodiments and configurations together also fall within the scope of the embodiments and the configurations according to the present disclosure.

```
                    SEQUENCE LISTINGS
                    sequence_156415.app Sequence ID: 1
Sequence length: 1677
Sequence type: DNA
Organism: Coccomyxa and its allied species, A
Sequence: 1
agtcatatgc ttgtctcaaa gattaagcca tgcatgtcta agtataaact gctttatact gtgaaactgc gaatggctca ttaaatcagt tatagtttat ttgatggtac cttactactc ggataaccgt agtaattcta gagctaatac gtgcgtaaat cccgacttct ggaagggacg tatttattag ataaaaggcc gaccggactc tgtccgactc gcggtgaatc atgataactc cacggatcgc atggcctcga gccggcgacg tttcattcaa atttctgccc tatcaacttt cgacggtaag gtattggctt accgtggtgg taacgggtga cggaggatta gggttcgatt ccggagaggg agcctgagaa acggctacca catccaagga aggcagcagg cgcgcaaatt acccaatctt gacacaagga ggtagtgaca ataaataaca ataccggggt ttttcaactc tggtaattgg aatgagtaca atctaaaccc cttaacgagg atcaattgga gggcaagtct ggtgccagca gccgcggtaa ttccagctcc aatagcgtat atttaagttg ttgcagttaa aaagctcgta gttggatttc gggcgggctc ggctggtccg cctatcggtg tgcactgacc gagcccgtct tgttgccggg gacgggctcc tgggcttaac tgtccgggac tcggagtcgg cgaggttact ttgagtaaat tagagtgttc aaagcaggcc tacgctctga atacattagc atggaataac acgataggac tctggcctat cttgttggtc tgtgggaccg gagtaatgat taagagggac agtcgggggc attcgtattt cattgtcaga ggtgaaattc ttggatttat gaaagacgaa ctactgcgaa agcatttgcc aaggatgttt tcattaatca agaacgaaag ttgggggctc gaagacgatt agataccgtc ctagtctcaa ccataaacga tgccgactag ggattggcgg gcgttctttt gatgacctcg ccagcaccttat gagaaatc aaagtttttg ggttccgggg ggagtatggt cgcaaggctg aaacttaaag gaattgacgg aagggcacca ccaggcgtgg agcctgcggc ttaatttgac tcaacacggg aaaacttacc aggtccagac atagtgagga ttgacagatt gagagctctt tcttgattct atgggtggtg gtgcatggcc
```

-continued

```
SEQUENCE LISTINGS
sequence_156415.app
```

```
gttcttagtt ggtgggttgc cttgtcaggt tgattccggt aacgaacgag acctcagcct gctaactagt cacggttggt tttaccagcc ggccgacttc ttagagggac tattggcgac tagccaatgg aagtgtgagg caataacagg tctgtgatgc ccttagatgt tctgggccgc acgcgcgcta cactgatgca atcaacgagc ctagccttgg ccgagaggtc cgggtaatct ttgaaactgc atcgtgatgg ggatagatta ttgcaattat taatcttcaa cgaggaatgc ctagtaagcg cgagtcatca gctcgcgttg attacgtccc tgcccttttgt acacaccgcc cgtcgctcct accgattggg tgtgctggtg aagcgttcgg attggcggct tcagggc
```

Sequence ID: 2
Sequence length: 1709
Sequence type: DNA
Organism: *Coccomyxa* and its allied species, B
Sequence: 2

```
agtcatatgc ttgtctcaaa gattaagcca tgcatgtcta agtataaact gctttatact gtgaaactgc gaatggctca ttaaatcagt tatagtttat ttgatggtac cttactactc ggataaccgt agtaattcta gagctaatac gtgcggaaat cccgacttct ggaagggacg tatttattag ataaaaggcc gaccgggctt gcccgaaacg cggtgaatca tgataactcc acgaatcgca tggcctcagc gccggcgatg tttcattcaa atttctgccc tatcaacttt cgacggtaag gtattggctt accgtggtgg taacgggtga cggaggatta gggttcgatt ccggagaggg agcctgagaa acggctacca catccaagga aggcagcagg cgcgcaaatt acccaatctt gacacaagga ggtagtgaca ataaataaca ataccggggt ttttcaactc tggtaattgg aatgagtaca atctaaaccc cttaacgagg atcaattgga gggcaagtct ggtgccagca gccgcggtaa ttccagctcc aatagcgtat atttaagttg ttgcagttaa aaagctcgta gttggatttc gggcgggccc ggccggtccg cctttgggtg tgcactgacc gggcccgtct tgttgccggg gacgggctcc tgggcttaac tgtccgggac tcggagtcgg cgaggttact ttgagtaaat tagagtgttc aaagcaggcc tacgctctga atacattagc atggaataac acgataggac tctggcctat cttgttggtc tgtgggaccg gagtaatgat taagagggac agtcggggc attcgtattt cattgtcaga ggtgaaattc ttggatttat gaaagacgaa ctactgcgaa agcatttgcc aaggatgttt tcattaatca agaacgaaag ttggggggctc gaagacgatt agataccgtc ctagtctcaa ccataaacga tgccgactag ggattggcgg gcgttctttt gatgaccccg ccagcacctt atgagaaatc aaagttttttg ggttccgggg ggagtatggt cgcaaggctg aaacttaaag gaattgacgg aagggcacca ccaggcgtgg agcctgcggc ttaatttgac tcaacacggg aaaacttacc aggtccagac atagtgagga ttgacagatt gagagctctt tcttgattct atgggtggtg gtgcatggcc gttcttagtt ggtgggttgc cttgtcaggt tgattccggt aacgaacgag acctcagcct gctaactagt cacgattggt tcttccagtc ggccgacttc ttagagggac tattggcgac tagccaatgg aagtgtgagg caataacagg tctgtgatgc ccttagatgt tctgggccgc acgcgcgcta cactgatgca atcaacgagc ctagccttgg ccgacaggtc cgggtaatct ttgaaactgc atcgtgatgg ggatagatga ttgcaattat tcatcttcaa cgaggaatgc ctagtaagcg cgagtcatca gctcgcgttg attacgtccc tgcccttttgt acacaccgcc
```

SEQUENCE LISTINGS
sequence_156415.app cgtcgctcct accgattggg tgtgctggtg aagcgttcgg attggcggca gtgcgcggtt cgccgctcgc tgcagccgag aagttcgtt Sequence ID: 3
Sequence length: 1714
Sequence type: DNA
Organism: *Coccomyxa* and its allied species, C
Sequence: 3
agtcatatgc ttgtctcaaa gattaagcca tgcatgtcta agtataaact gctttatact gtgaaactgc gaatggctca ttaaatcagt tatagtttat ttgatggtac cttactactc ggataaccgt agtaattcta gagctaatac gtgcggaaat cccgacttct ggaagggacg tatttattag ataaaaggcc gacccgggctt gcccgaaacg cggtgaatca tgataactcc acgaatcgca tggcctcagt gccggcgatg tttcattcaa atttctgccc tatcaacttt cgacggtaag gtattggctt accgtggtgg taacgggtga cggaggatta gggttcgatt ccggagaggg agcctgagaa acggctacca catccaagga aggcagcagg cgcgcaaatt acccaatctt gacacaagga ggtagtgaca ataaataaca ataccggggt ttttcaactc tggtaattgg aatgagtaca atctaaaccc cttaacgagg atcaattgga gggcaagtct ggtgccagca gccgcggtaa ttccagctcc aatagcgtat atttaagttg ttgcagttaa aaagctcgta gttggatttc gggcgggccc ggccggtccg ccttctggtg tgcactgacc gggcccgtct tgttgccggg gacggctcc tgggcttaac tgtccgggac tcggagtcgg cgaggttact ttgagtaaat tagagtgttc aaagcaggcc tacgctctga atacattagc atggaataac acgataggac tctggcctat cttgttggtc tgtgggaccg gagtaatgat taagagggac agtcggggc attcgtattt cattgtcaga ggtgaaattc ttggatttat gaaagacgaa ctactgcgaa agcatttgcc aaggatgttt tcattaatca agaacgaaag ttgggggctc gaagacgatt agataccgtc ctagtctcaa ccataaacga tgccgactag ggattggcgg gcgttctttt gatgaccccg ccagcacctt atgagaaatc aaagtttttg ggttccgggg ggagtatggt cgcaaggctg aaacttaaag gaattgacgg aagggcacca ccaggcgtgg agcctgcggc ttaatttgac tcaacacggg aaaacttacc aggtccagac atagtgagga ttgacagatt gagagctctt tcttgattct atgggtggtg gtgcatggcc gttcttagtt ggtgggttgc cttgtcaggt tgattccggt aacgaacgag acctcagcct gctaactagt cacgattggt tcttccagtc ggccgacttc ttagagggac tattggcgac tagccaatgg aagtgtgagg caataacagg tctgtgatgc ccttagatgt tctgggccgc acgcgcgcta cactgatgca atcaacgagc ctagccttgg ccgacaggtc cgggtaatct ttgaaactgc atcgtgatgg ggatagatga ttgcaattat tcatcttcaa cgaggaatgc ctagtaagcg cgagtcatca gctcgcgttg attacgtccc tgccctttgt acacaccgcc cgtcgctcct accgattggg tgtgctggtg aagcgttcgg attggcggca gtgcgcggtt cgccgctcgc tgcagccgag aagttcgtta aacc Sequence ID: 4
Sequence length: 1753
Sequence type: DNA
Organism: *Watanabea Glade* and its allied species, D
Sequence: 4
gtcctgccag tagtcatatg cttgtctcaa agattaagcc atgcatgtcc aagtatgaac tgcttatact gtgaaactgc gaatggctca ttaaatcagt tatagtttat ttgatggtac

```
ctggctactc ggatacccgt agtaattcta gagctaatac gtgcgcacat cccgactctg tggaagggac gtatttatta gataaaaggc cgaccgggct tgcccgactc gcggcgaatc atgataactc cacgaatcgc acggcctccg cgccggcgat gtttcattca aatttctgcc ctatcaactt tcgatggtag gatagaggcc taccatggtt ttgacgggtg acggggaatt agggttctat gccggagagg gagcctgaga acggctacc acatccaagg aaggcagcag gcgcgcaaat tacccaatcc cgacacgggg aggtagtgac aataaataac aataccgggc tcttacgagt ctggtgattg aatgagaac aatctaaatc ccttaacgag gatcgattgg agggcaagtc tggtgccagc agccgcggta attccagctc caatagcgta tatttaagtt gttgcagtta aaaagctcgt agtcggatgt cgggcggcct ccgtcggtcc gccgatcggc gtgcaccggc ggggcgccgc ctcgctgccg gggacgggcg cctgggcttc actgtcccgg gccccggagt cggcgaggtc actttgagta aattagagtg ttcaaagcag gcagccgctc tgaatacgcc agcatggaat gacgcgatag gactctgggc ctattccgtc ggtctgtggg accggagtaa tgatgaacag ggacggtcgg gggcattcgt atttcgctgt cagaggtgaa attcttggat ttgcgaaaga cggacttctg cgaaagcatt tgccaaggat gttttcattg atcaagaacg aaagtcgggg gctcgaagac gattagatac cgtcctagtc tcgaccataa acgatgccga ctagggatcg gcgggcgttt cttcgacgac cccgccggca cctcacgaga aatcaaagtg ttcgggttcc gggggagta tggtcgcaag gctgaaactt aaaggaattg acggaagggc accaccaggc gtggagcctg cggcttaatt tgactcaaca cgggaaaact taccaggtcc agacatagcg aggattgaca gattgacagc tctttcttga ttctatgggt ggtggtgcat ggccgttctt agttggtggg ttgccttgtc aggttgattc cggtaacgaa cgagacctcg gcctgctaaa tagccccggg cggcgttcgc gccggccggc cgagcttctt agagggactc tcggcgacta gccgatggaa gtgcgaggca ataacaggtc tgtgatgccc ttagatgttc tgggccgcac gcgcgctaca ctgacgcagc caacgggcgc agccttggcc gagaggcccg ggtaatccgg cagcctgcgt cgtgacgggg ctagactctt gcaattatca gtcttcaacg aggaatgcct agtaggcgcg agtcatcagc tcgcgtcgat tacgtccctg cccttttgtac acaccgcccg tcgctcctac cgattggatg tgctggtgaa gcgctcggac cggccgcgtc gcgcggttcg ccgcgcctcg cagccgggaa gtccgttgaa ccctcccacc taggggaagg aga
```

Sequence ID: 5
Sequence length: 1764
Sequence type: DNA
Organism: *Watanabea Glade* and its allied species, E
Sequence: 5

```
tttatcctgc cagtagtcat atgcttgtct caaagactaa gccatgcatg tgtaagtatg aatcgctcat acggtgaaac tgcgaatggc tcattaaatc agttatcgtt tatttgatgg tactgcccta ctcggataac cgttggaaat cattggctaa tacgtgcgca catcccgact ctcggaaggg acgtatttat tagatagaag accgaccggg cctcggcccg agctgcggtg aatcatgata acttcacgaa tcgcatggcc ccgcgccggc gatgtttcat tcaaatttct gccctatcaa ctttcgatgg taggatagag gcctaccatg gttttgacgg gtgacggagt tttcgggaac ggctccggag aggccgcctg aggaacagcg accatttcca aggaaagcag
```

-continued

SEQUENCE LISTINGS
sequence_156415.app caggcgcgca aattacccaa tcccgacacg gggaggtagt gacaataaat aacaataccg ggcttttttca agtctggtga ttggaatgag tacaatctaa atcccttaac gaggatcaat tggagggcaa gtctggtgcc agcagccgcg gtaattccag ctccaatagc gtatatttaa gttgttgcag ttaaaaagct cgtagttgga tctagacgag gccccgccgg tccgccgtca ggtgtgcact ggcgtgggcc cgccttgctg tcggggacgg gctcctgggc ttcgctgtcc gggacccgga gtcgacgagg ttactttgag taaattagag tgttcaaagc aggcctacgc tctgaatacg ttagcatgga ataacacgat aggactctgg cctatcctgt tggtctgtgg gaccggagta atgattaaga gggacggtcg ggggcattcg tatttcgttg tcagaggtga aattcttgga ttttacaaaa agacggactt ctgcgaaagc atttgccaag gatgttttca ttaatcaaga acgaaatttg gggggctcga gacgattaga taccgtccta gtctcaaccc ataaacgatg ccgactaggg atcggcgggt gttgaatcga tgaccccgcc ggcacctcac gagaaatcaa agtctttggg ttccgggggg agtatggttg caaggctgaa acttaaagga attgacggaa gggcaccacc aggcgtggag cctgcggctt aatttgactc aacacgggaa aacttaccag gtccagacat agtgaggatt gacagattga cagctctttc ttgattctgt gggtggtggt gcatggccgt tcttagttgg tgggttgcct tgtctgccta atcgcgataa acggacgaga ccccggcctg ctaaatagcc acggtcggcg tcccgccggc cggcgggctt cttagaggga ctatcggcat ttagccggag gaagtgcggg gcaataacag gtctgtgatg cccttagatg ttctgggcgg cacgcgcgct acactggtgc gatcagcgag cctagcctcg gccgagaggt ccgggtaatc ttgcaaaccg caccgtgatg gggctagact cttgcaatta tcagtcttca acgaggaatg cctagtaagc gcgagtcatc agctcgtgct gattacgtcc ctgcccttttg tacacaccgc ccgtcgctcc taccgattgg atgtgctggt gaagcgttcg gactggcggc gcgggcggct cgttcgcctg gcgccgccgg gaagttcgtt gaaccctccc acctaaagga aggagaagtc gtaa Sequence ID: 6
Sequence length: 2205
Sequence type: DNA
Organism: *Watanabea clade* and its allied species, F
Sequence: 6
gtcatatgct gtctcaaaga ttaagccatg catgtccaag tatgaactgc ttatactgtg aaactgcgaa tggctcatta aatcagttat agtttatttg atggtacctg gctactcgga taccgtagt aattctagag ctaatacgtg cgcacatccc gactctgtgg aagggacgta tttattagat aaaaggccga ccgggcttgc ccgactcgcg gcgaatcatg ataactccac gaatcgcacg gcctccgcgc cggcgatgtt tcattcaaat ttctgcccta tcaactttcg atggtaggat agaggcctac catggttttg acgggtgacg gggaattagg gttctatgcc ggagagggag cctgagaaac ggctaccaca tccaaggaag gcagcaggcg cgcaaattac ccaatcccga cacggggagg tagtgacaat aaataacaat accgggctct tacgagtctg gtgattggaa tgagaacaat ctaaatccct taacgaggat cgattggagg gcaagtctgg tgccagcagc cgcggtaatt ccagctccaa tagcgtatat ttaagttgtt gcagttaaaa agctcgtagt cggatgtcgg gcggcctccg tcggtccgcc gatcggcgtg caccggcggg gcgccgcctc gctgccgggg acgggcgcct gggcttcact gtcccgggcc ccggagtcgg cgaggtcact ttgagtaaat tagagtgttc aaagcaggca gccgctctga atacgccagc

```
atggaatgac gcgataggac tctggcctat tccgtcggtc tgtgggaccg gagtaatgat gaacagggac ggtcggggc attcgtattt cgctgtcaga ggtgaaattc ttggatttgc gaaagacgga cttctgcgaa agcatttgcc aaggatgttt tcattgatca agaacgaaag tcggggctc gaagacgatt agataccgtc ctagtctcga ccataaacga tgccgactag ggatcggcgg gcgtttcttc gacgaccccg ccggcacctc acgagaaatc aaagtgttcg ggttccgggg ggagtatggt cgcaaggctg aaacttaaag gaattgacgg aagggcacca ccaggcgttt gaccggctct ggcgcctcag agtggcggcc gcgaggccgc cgctagtggc cccgccctcg ggcgggaccg cgacactgtc aaattgcggg gacctcctaa agcttcgggt gccaagccca gcccggaaac gggcgggtgg ccggggagag agccccgggg tacggcgaca agcccggaga tgcgacaatg gacgacccgc agccaagtcc tgaggggcgc cgcacgccgg cgcccacgga tgcagttcac agactaaatg gcagtgggcc cgtcgcctgc gggtggaacc ggtcgatggc ggtctgcgtc atccgactga tccgccggcg acgcggctta agatatagtc ggccctcagc cgagaggctg acccgtcgga ggaaggctgc cctgagcggc gcctgagagc cgggcgggag ggccctcccc acgcgaggag ggccccggac cagcgggagc ctgcggctta atttgactca acacgggaaa acttaccagg tccagacata gcgaggattg acagattgac agctctttct tgattctatg ggtggtggtg catggccgtt cttagttggt gggttgcctt gtcaggttga ttccggtaac gaacgagacc tcggcctgct aaatagcccc gggcggcgtt cgcgccggcc ggccgagctt cttagaggga ctctcggcga ctagccgatg aagtgcgag gcaataacag gtcgtgatgg cccttagatg ttctgggccg cacgcgcgct acactgacgc agccaacggg cgcagccttg gccgagaggc ccgggtaatc cggcagcctg cgtcgtgacg gggctagact cttgcaatta tcagtctttc aacgaggaat gcctagtagg cgcgagtcat cagctcgcgt cgattacgtc cctgcccttt gtacacaccg cccgtcgctc ctaccgattg gatgtgctgg tgaagcgctc ggaccggccg cgtcgcgcgg ttcgccgcgc ctcgcagccg ggaagtccgt tgaaccctcc cacctagggg aaggagaagt cgtaa
```

What is claimed is:

1. A culture method for microalgae comprising:
preparing culture liquid including ammonia nitrogen, a pH of the culture liquid being equal to or less than 4;
adjusting the pH of the culture liquid to a predetermined value before inoculation of a microalgae;
culturing, in a raceway culture tank containing the culture liquid, microalgae of a genus *Coccomyxa* or a genus *Pseudococcomyxa* in an outdoor open culture system in a range of 15-35 degrees Celsius,
insolating the raceway culture tank by using the sun as a light source during the culturing; and
continuously introducing $CO_2$ into the raceway culture tank through an introduction portion of the raceway culture tank during culturing.

2. The culture method for microalgae according to claim 1, further comprising:
recovering the microalgae from the culture liquid used in the culturing of the microalgae, and
newly culturing the microalgae with the culture liquid after recovery in the outdoor open culture system in a culture condition identical with the culture method for microalgae.

3. The culture method for microalgae according to claim 1,
wherein:
the microalgae of the genus *Coccomyxa* is provided by *Coccomyxa* simplex, *Coccomyxa* chodatii, or a combination of *Coccomyxa* simplex and *Coccomyxa* chodatii;
the microalgae of the genus *Pseudococcomyxa* is provided by Pseudochoricystis ellipsoidea N1 strain, Pseudochoricystis ellipsoidea Obi strain, or a combination of Pseudochoricystis ellipsoidea N1 strain and Pseudochoricystis ellipsoidea Obi strain; and
the ammonia nitrogen is provided by urea.

4. The culture method for microalgae according to claim 1, wherein:
the pH of the culture liquid is not adjusted during the culturing.

5. An open culture system used in the culture method in an outdoor open system for the microalgae according to claim 1, the open culture system comprising:
a detector detecting one or more parameters selected from a parameter group only including pH, $CO_2$ concentration, and concentration of algae in the culture liquid; and
a controller controlling the one or more parameters within a respective predetermined range.

6. The open culture system according to claim 5, wherein:
the one or more parameters include the pH; and
the predetermined range of the pH corresponds to 4 or less.

7. The open culture system according to claim 5, wherein:
the one or more parameters include the $CO_2$ concentration; and
the predetermined range of the $CO_2$ concentration corresponds to 7.45-74.5 mg/L.

8. The open culture system according to claim 5, further comprising:
a feeder that introduces a pH adjuster into the culture liquid; and
an introduction portion that introduces $CO_2$ into the culture liquid,
wherein:
the detector detects pH and $CO_2$ concentration at least;
the predetermined range of pH is set to 3-4;
the predetermined range of the $CO_2$ concentration corresponds to 7.45-74.5 mg/L; and
the controller controls the feeder and the introduction portion so that pH is adjusted within 3-4 and the $CO_2$ concentration is adjusted within 7.45-74.5 mg/L.

9. The open culture system according to claim 8, wherein:
the predetermined range of the concentration of algae corresponds to 2.5 or less in measurement by OD720.

10. An open culture system comprising:
a raceway culture tank;
a detector that is placed at the raceway culture tank and detects at least one parameter including pH, $CO_2$ concentration, and concentration of algae in a culture liquid, the at least one parameter configuring a parameter group; and
a controller that controls the at least one parameter in a respective predetermined range,
wherein:
pH of the culture liquid is 4 or less;
the culture liquid includes urea as ammonia nitrogen;
the open culture system cultures a microalgae of a genus *Coccomyxa* or of a genus *Pseudococcomyxa* under insolation by sun in a range of 15-35 degrees Celsius.

11. The open culture system according to claim 10, wherein:
the predetermined range of the concentration of algae corresponds to 2.5 or less in measurement by OD720.

* * * * *

SEQUENCE LISTING

<160> NUMBER OF SEQ ID NOS: 6

<210> SEQ ID NO 1
<211> LENGTH: 1677
<212> TYPE: DNA
<213> ORGANISM: Artificial Sequence
<220> FEATURE:
<223> OTHER INFORMATION: Coccomyxa and its allied species, A

<400> SEQUENCE: 1

```
agtcatatgc ttgtctcaaa gattaagcca tgcatgtcta agtataaact gctttatact      60
gtgaaactgc gaatggctca ttaaatcagt tatagtttat ttgatggtac cttactactc     120
ggataaccgt agtaattcta gagctaatac gtgcgtaaat cccgacttct ggaagggacg     180
tatttattag ataaaaggcc gaccggactc tgtccgactc gcggtgaatc atgataactc     240
cacggatcgc atggcctcga gccggcgacg tttcattcaa atttctgccc tatcaacttt     300
```

```
cgacggtaag gtattggctt accgtggtgg taacgggtga cggaggatta gggttcgatt      360
ccggagaggg agcctgagaa acggctacca catccaagga aggcagcagg cgcgcaaatt      420
acccaatctt gacacaagga ggtagtgaca ataaataaca ataccggggt ttttcaactc      480
tggtaattgg aatgagtaca atctaaaccc cttaacgagg atcaattgga gggcaagtct      540
ggtgccagca gccgcggtaa ttccagctcc aatagcgtat atttaagttg ttgcagttaa      600
aaagctcgta gttggatttc gggcgggctc ggctggtccg cctatcggtg tgcactgacc      660
gagcccgtct tgttgccggg gacgggctcc tgggcttaac tgtccgggac tcggagtcgg      720
cgaggttact ttgagtaaat tagagtgttc aaagcaggcc tacgctctga atacattagc      780
atggaataac acgataggac tctggcctat cttgttggtc tgtgggaccg gagtaatgat      840
taagagggac agtcggggc attcgtattt cattgtcaga ggtgaaattc ttggatttat       900
gaaagacgaa ctactgcgaa agcatttgcc aaggatgttt tcattaatca agaacgaaag      960 ttggggctc gaagacgatt agataccgtc ctagtctcaa ccataaacga tgccgactag      1020
ggattggcgg gcgttctttt gatgacctcg ccagcacctt atgagaaatc aaagtttttg     1080
ggttccgggg ggagtatggt cgcaaggctg aaacttaaag gaattgacgg aagggcacca     1140
ccaggcgtgg agcctgcggc ttaatttgac tcaaacgggg aaaacttacc aggtccagac     1200
atagtgagga ttgacagatt gagagctctt tcttgattct atgggtggtg gtgcatggcc     1260
gttcttagtt ggtgggttgc cttgtcaggt tgattccggt aacgaacgag acctcagcct     1320
gctaactagt cacggttggt tttaccagcc ggccgacttc ttagagggac tattggcgac     1380
tagccaatgg aagtgtgagg caataacagg tctgtgatgc ccttagatgt tctgggccgc     1440
acgcgcgcta cactgatgca atcaacgagc ctagccttgg ccgagaggtc cgggtaatct     1500
ttgaaactgc atcgtgatgg ggatagatta ttgcaattat taatcttcaa cgaggaatgc     1560
ctagtaagcg cgagtcatca gctcgcgttg attacgtccc tgccctttgt acacaccgcc     1620
cgtcgctcct accgattggg tgtgctggtg aagcgttcgg attggcggct tcagggc        1677

<210> SEQ ID NO 2
<211> LENGTH: 1709
<212> TYPE: DNA
<213> ORGANISM: Artificial Sequence
<220> FEATURE:
<223> OTHER INFORMATION: Coccomyxa and its allied species, B

<400> SEQUENCE: 2
agtcatatgc ttgtctcaaa gattaagcca tgcatgtcta agtataaact gctttatact       60
gtgaaactgc gaatggctca ttaaatcagt tatagtttat ttgatggtac cttactactc      120
ggataaccgt agtaattcta gagctaatac gtgcggaaat cccgacttct ggaagggacg      180
tatttattag ataaaaggcc gaccgggctt gcccgaaacg cggtgaatca tgataactcc      240
acgaatcgca tggcctcagc gccggcgatg tttcattcaa atttctgccc tatcaacttt      300
cgacggtaag gtattggctt accgtggtgg taacgggtga cggaggatta gggttcgatt      360
ccggagaggg agcctgagaa acggctacca catccaagga aggcagcagg cgcgcaaatt      420
acccaatctt gacacaagga ggtagtgaca ataaataaca ataccggggt ttttcaactc      480
tggtaattgg aatgagtaca atctaaaccc cttaacgagg atcaattgga gggcaagtct      540
ggtgccagca gccgcggtaa ttccagctcc aatagcgtat atttaagttg ttgcagttaa      600
aaagctcgta gttggatttc gggcgggccc ggccggtccg cctttgggtg tgcactgacc      660
gggcccgtct tgttgccggg gacgggctcc tgggcttaac tgtccgggac tcggagtcgg      720
```

```
cgaggttact ttgagtaaat tagagtgttc aaagcaggcc tacgctctga atacattagc        780
atggaataac acgataggac tctggcctat cttgttggtc tgtgggaccg gagtaatgat        840
taagagggac agtcggggc attcgtattt cattgtcaga ggtgaaattc ttggatttat         900
gaaagacgaa ctactgcgaa agcatttgcc aaggatgttt tcattaatca agaacgaaag        960
ttgggggctc gaagacgatt agataccgtc ctagtctcaa ccataaacga tgccgactag       1020
ggattggcgg gcgttctttt gatgaccccg ccagcacctt atgagaaatc aaagtttttg       1080
ggttccgggg ggagtatggt cgcaaggctg aaacttaaag gaattgacgg aagggcacca       1140
ccaggcgtgg agcctgcggc ttaatttgac tcaacacggg aaaacttacc aggtccagac       1200
atagtgagga ttgacagatt gagagctctt tcttgattct atgggtggtg gtgcatggcc       1260
gttcttagtt ggtggggttgc cttgtcaggt tgattccggt aacgaacgag acctcagcct       1320
gctaactagt cacgattggt tcttccagtc ggccgacttc ttagagggac tattggcgac       1380
tagccaatgg aagtgtgagg caataacagg tctgtgatgc ccttagatgt tctgggccgc       1440
acgcgcgcta cactgatgca atcaacgagc ctagccttgg ccgacaggtc cgggtaatct       1500
ttgaaactgc atcgtgatgg ggatagatga ttgcaattat tcatcttcaa cgaggaatgc       1560
ctagtaagcg cgagtcatca gctcgcgttg attacgtccc tgcccttttgt acacaccgcc      1620 cgtcgctcct accgattggg tgtgctggtg aagcgttcgg attggcggca gtgcgcggtt       1680
cgccgctcgc tgcagccgag aagttcgtt                                         1709

<210> SEQ ID NO 3
<211> LENGTH: 1714
<212> TYPE: DNA
<213> ORGANISM: Artificial Sequence
<220> FEATURE:
<223> OTHER INFORMATION: Coccomyxa and its allied species,C

<400> SEQUENCE: 3
agtcatatgc ttgtctcaaa gattaagcca tgcatgtcta agtataaact gctttatact         60
gtgaaactgc gaatggctca ttaaatcagt tatagtttat ttgatggtac cttactactc        120
ggataaccgt agtaattcta gagctaatac gtgcggaaat cccgacttct ggaagggacg        180
tatttattag ataaaaggcc gaccgggctt gcccgaaacg cggtgaatca tgataactcc        240
acgaatcgca tggcctcagt gccggcgatg tttcattcaa atttctgccc tatcaacttt        300
cgacggtaag gtattggctt accgtggtgg taacgggtga cggaggatta gggttcgatt        360
ccggagaggg agcctgagaa acggctacca catccaagga aggcagcagg cgcgcaaatt       420
acccaatctt gacacaagga ggtagtgaca ataaataaca ataccggggt ttttcaactc        480
tggtaattgg aatgagtaca atctaaaccc cttaacgagg atcaattgga gggcaagtct       540
ggtgccagca gccgcggtaa ttccagctcc aatagcgtat atttaagttg ttgcagttaa       600
aaagctcgta gttggatttc gggcgggcc ggccggtccg ccttctggtg tgcactgacc        660
gggcccgtct tgttgccggg gacgggctcc tgggcttaac tgtccgggac tcggagtcgg      720
cgaggttact ttgagtaaat tagagtgttc aaagcaggcc tacgctctga atacattagc       780
atggaataac acgataggac tctggcctat cttgttggtc tgtgggaccg gagtaatgat       840
taagagggac agtcggggc attcgtattt cattgtcaga ggtgaaattc ttggatttat        900
gaaagacgaa ctactgcgaa agcatttgcc aaggatgttt tcattaatca agaacgaaag       960
ttgggggctc gaagacgatt agataccgtc ctagtctcaa ccataaacga tgccgactag      1020
```

```
ggattggcgg gcgttctttt gatgaccccg ccagcacctt atgagaaatc aaagttttg      1080 ggttccgggg ggagtatggt cgcaaggctg aaacttaaag gaattgacgg aagggcacca      1140
ccaggcgtgg agcctgcggc ttaatttgac tcaacacggg aaaacttacc aggtccagac      1200
atagtgagga ttgacagatt gagagctctt tcttgattct atgggtggtg gtgcatggcc      1260
gttcttagtt ggtgggttgc cttgtcaggt tgattccggt aacgaacgag acctcagcct      1320
gctaactagt cacgattggt tcttccagtc ggccgacttc ttagagggac tattggcgac      1380
tagccaatgg aagtgtgagg caataacagg tctgtgatgc ccttagatgt tctgggccgc      1440
acgcgcgcta cactgatgca atcaacgagc tagccttgg ccgacaggtc cgggtaatct       1500
ttgaaactgc atcgtgatgg ggatagatga ttgcaattat tcatcttcaa cgaggaatgc      1560
ctagtaagcg cgagtcatca gctcgcgttg attacgtccc tgccctttgt acacaccgcc      1620
cgtcgctcct accgattggg tgtgctggtg aagcgttcgg attggcggca gtgcgcggtt      1680
cgccgctcgc tgcagccgag aagttcgtta aacc                                  1714

<210> SEQ ID NO 4
<211> LENGTH: 1753
<212> TYPE: DNA
<213> ORGANISM: Artificial Sequence
<220> FEATURE:
<223> OTHER INFORMATION: Watanabea clade and its allied species,D

<400> SEQUENCE: 4
gtcctgccag tagtcatatg cttgtctcaa agattaagcc atgcatgtcc aagtatgaac        60
tgcttatact gtgaaactgc gaatggctca ttaaatcagt tatagtttat ttgatggtac       120
ctggctactc ggataccgt agtaattcta gagctaatac gtgcgcacat cccgactctg        180
tggaagggac gtatttatta gataaaaggc cgaccgggct tgcccgactc gcggcgaatc       240
atgataactc cacgaatcgc acggcctccg cgccggcgat gtttcattca aatttctgcc      300
ctatcaactt tcgatggtag gatagaggcc taccatggtt ttgacgggtg acggggaatt      360
agggttctat gccggagagg gagcctgaga acggctacc acatccaagg aaggcagcag       420
gcgcgcaaat tacccaatcc cgacacgggg aggtagtgac aataaataac aataccgggc      480
tcttacgagt ctggtgattg gaatgagaac aatctaaatc ccttaacgag gatcgattgg      540
agggcaagtc tggtgccagc agccgcggta attccagctc caatagcgta tatttaagtt      600
gttgcagtta aaaagctcgt agtcggatgt cgggcggcct ccgtcggtcc gccgatcggc      660
gtgcaccggc gggcgccgc ctcgctgccg gggacgggcg cctgggcttc actgtcccgg       720
gccccggagt cggcgaggtc actttgagta aattagagtg ttcaaagcag gcagccgctc      780
tgaatacgcc agcatggaat gacgcgtag gactctgggc ctattccgtc ggtctgtggg       840
accggagtaa tgatgaacag ggacggtcgg gggcattcgt atttcgctgt cagaggtgaa      900
attcttggat ttgcgaaaga cggacttctg cgaaagcatt gccaaggat gttttcattg       960 atcaagaacg aaagtcgggg gctcgaagac gattagatac cgtcctagtc tcgaccataa     1020
acgatgccga ctagggatcg gcgggcgttt cttcgacgac cccgccggca cctcacgaga     1080
aatcaaagtg ttcgggttcc gggggagta tggtcgcaag gctgaaactt aaaggaattg      1140
acggaagggc accaccaggc gtggagcctg cggcttaatt tgactcaaca cgggaaaact    1200
taccaggtcc agacatagcg aggattgaca gattgacagc tctttcttga ttctatgggt     1260
ggtggtgcat ggccgttctt agttggtggg ttgccttgtc aggttgattc cggtaacgaa     1320
cgagacctcg gcctgctaaa tagccccggg cggcgttcgc gccggccggc cgagcttctt     1380
```

| | |
|---|---|
| agagggactc tcggcgacta gccgatggaa gtgcgaggca ataacaggtc tgtgatgccc | 1440 |
| ttagatgttc tgggccgcac gcgcgctaca ctgacgcagc caacgggcgc agccttggcc | 1500 |
| gagaggcccg ggtaatccgg cagcctgcgt cgtgacgggg ctagactctt gcaattatca | 1560 |
| gtcttcaacg aggaatgcct agtaggcgcg agtcatcagc tcgcgtcgat tacgtccctg | 1620 |
| ccctttgtac acaccgcccg tcgctcctac cgattggatg tgctggtgaa gcgctcggac | 1680 |
| cggccgcgtc gcgcggttcg ccgcgcctcg cagccgggaa gtccgttgaa ccctcccacc | 1740 |
| tagggaagg aga | 1753 |

<210> SEQ ID NO 5
<211> LENGTH: 1764
<212> TYPE: DNA
<213> ORGANISM: Artificial Sequence
<220> FEATURE:
<223> OTHER INFORMATION: Watanabea clade and its allied species, E

<400> SEQUENCE: 5

| | |
|---|---|
| tttatcctgc cagtagtcat atgcttgtct caaagactaa gccatgcatg tgtaagtatg | 60 |
| aatcgctcat acggtgaaac tgcgaatggc tcattaaatc agttatcgtt tatttgatgg | 120 |
| tactgcccta ctcggataac cgttggaaat cattggctaa tacgtgcgca catcccgact | 180 |
| ctcggaaggg acgtatttat tagatagaag accgaccggg cctcggcccg agctgcggtg | 240 |
| aatcatgata acttcacgaa tcgcatggcc ccgcgccggc gatgtttcat tcaaatttct | 300 |
| gccctatcaa ctttcgatgg taggatagag gcctaccatg gttttgacgg gtgacggagt | 360 |
| tttcgggaac ggctccggag aggccgcctg aggaacagcg accatttcca aggaaagcag | 420 |
| caggcgcgca aattacccaa tcccgacacg gggaggtagt gacaataaat aacaataccg | 480 |
| ggcttttca gtctggtga ttggaatgag tacaatctaa atcccttaac gaggatcaat | 540 |
| tggagggcaa gtctggtgcc agcagccgcg gtaattccag ctccaatagc gtatatttaa | 600 |
| gttgttgcag ttaaaaagct cgtagttgga tctagacgag gccccgccgg tccgccgtca | 660 |
| ggtgtgcact ggcgtgggcc cgccttgctg tcggggacgg gctcctgggc ttcgctgtcc | 720 |
| gggacccgga gtcgacgagg ttactttgag taaattagag tgttcaaagc aggcctacgc | 780 |
| tctgaatacg ttagcatgga ataacacgat aggactctgg cctatcctgt tggtctgtgg | 840 |
| gaccggagta atgattaaga gggacggtcg ggggcattcg tatttcgttg tcagaggtga | 900 |
| aattcttgga ttttacaaaa agacggactt ctgcgaaagc atttgccaag gatgttttca | 960 |
| ttaatcaaga acgaaatttg gggggctcga gacgattaga taccgtccta gtctcaaccc | 1020 |
| ataaacgatg ccgactaggg atcggcgggt gttgaatcga tgaccccgcc ggcacctcac | 1080 |
| gagaaatcaa agtctttggg ttccgggggg agtatggttg caaggctgaa acttaaagga | 1140 |
| attgacggaa gggcaccacc aggcgtggag cctgcggctt aatttgactc aacacgggaa | 1200 |
| aacttaccag gtccagacat agtgaggatt gacagattga cagctctttc ttgattctgt | 1260 |
| gggtggtggt gcatggccgt tcttagttgg tgggttgcct tgtctgccta atcgcgataa | 1320 |
| acggacgaga ccccggcctg ctaaatagcc acggtcggcg tccgccggc cggcgggctt | 1380 |
| cttagaggga ctatcggcat ttagccgag gaagtgcggg gcaataacag gtctgtgatg | 1440 |
| cccttagatg ttctgggcgg cacgcgcgct acactggtgc gatcagcgag cctagcctcg | 1500 |
| gccgagaggt ccgggtaatc ttgcaaaccg caccgtgatg gggctagact cttgcaatta | 1560 |
| tcagtcttca acgaggaatg cctagtaagc gcgagtcatc agctcgtgct gattacgtcc | 1620 |

| ctgcccttg tacacaccgc cgtcgctcc taccgattgg atgtgctggt gaagcgttcg | 1680 |
| gactggcggc gcgggcggct cgttcgcctg gcgccgccgg aagttcgtt gaaccctccc | 1740 |
| acctaaagga aggagaagtc gtaa | 1764 |

<210> SEQ ID NO 6
<211> LENGTH: 2205
<212> TYPE: DNA
<213> ORGANISM: Artificial Sequence
<220> FEATURE:
<223> OTHER INFORMATION: Watanabea clade and its allied species,F

<400> SEQUENCE: 6

| gtcatatgct gtctcaaaga ttaagccatg catgtccaag tatgaactgc ttatactgtg | 60 |
| aaactgcgaa tggctcatta atcagttat agtttatttg atggtacctg gctactcgga | 120 |
| tacccgtagt aattctagag ctaatacgtg cgcacatccc gactctgtgg aagggacgta | 180 |
| tttattagat aaaaggccga ccgggcttgc ccgactcgcg gcgaatcatg ataactccac | 240 |
| gaatcgcacg gcctccgcgc cggcgatgtt tcattcaaat ttctgcccta tcaactttcg | 300 |
| atggtaggat agaggcctac catggttttg acgggtgacg gggaattagg gttctatgcc | 360 |
| ggagagggag cctgagaaac ggctaccaca tccaaggaag gcagcaggcg cgcaaattac | 420 |
| ccaatcccga cacggggagg tagtgacaat aaataacaat accgggctct tacgagtctg | 480 |
| gtgattggaa tgagaacaat ctaaatccct taacgaggat cgattggagg gcaagtctgg | 540 |
| tgccagcagc cgcggtaatt ccagctccaa tagcgtatat ttaagttgtt gcagttaaaa | 600 |
| agctcgtagt cggatgtcgg gcggcctccg tcggtccgcc gatcggcgtg caccggcggg | 660 |
| gcgccgcctc gctgccgggg acgggcgcct gggcttcact gtcccgggcc ccggagtcgg | 720 |
| cgaggtcact ttgagtaaat tagagtgttc aaagcaggca gccgctctga atacgccagc | 780 |
| atggaatgac gcgataggac tctggcctat tccgtcggtc tgtgggaccg gagtaatgat | 840 |
| gaacagggac ggtcggggc attcgtattt cgctgtcaga ggtgaaattc ttggatttgc | 900 |
| gaaagacgga cttctgcgaa agcatttgcc aaggatgttt tcattgatca agaacgaaag | 960 |
| tcggggctc gaagacgatt agataccgtc ctagtctcga ccataaacga tgccgactag | 1020 |
| ggatcggcgg gcgtttcttc gacgaccccg ccggcacctc acgagaaatc aaagtgttcg | 1080 |
| ggttccgggg ggagtatggt cgcaaggctg aaacttaaag gaattgacgg aagggcacca | 1140 |
| ccaggcgttt gaccggctct ggcgcctcag agtggcggcc gcgaggccgc gctagtggc | 1200 |
| cccgccctcg ggcgggaccg cgacactgtc aaattgcggg gacctcctaa agcttcgggt | 1260 |
| gccaagccca gcccggaaac gggcgggtgg ccggggagag agcccccggg tacggcgaca | 1320 |
| agcccggaga tgcgacaatg gacgaccgc agccaagtcc tgaggggcgc cgcacgccgg | 1380 |
| cgcccacgga tgcagttcac agactaaatg gcagtgggcc cgtcgcctgc gggtggaacc | 1440 |
| ggtcgatggc ggtctgcgtc atccgactga tccgccggcg acgcggctta agatatagtc | 1500 |
| ggccctcagc cgagaggctg acccgtcgga ggaaggctgc cctgagcggc gcctgagagc | 1560 |
| cgggcgggag ggccctcccc acgcgaggag ggccccggac cagcgggagc ctgcggctta | 1620 |
| atttgactca acacgggaaa acttaccagg ccagacatag cgaggattga acagattgac | 1680 |
| agctcttct tgattctatg ggtggtggtg catggccgtt cttagttggt gggttgcctt | 1740 |
| gtcaggttga ttccggtaac gaacgagacc tcggcctgct aaatagcccc gggcggcgtt | 1800 |
| cgcgccggcc ggccgagctt cttagaggga ctctcggcga ctagccgatg gaagtgcgag | 1860 |
| gcaataacag gtctgtgatg cccttagatg ttctgggccg cacgcgcgct acactgacgc | 1920 |

| | | | | |
|---|---|---|---|---|
| agccaacggg | cgcagccttg | gccgagaggc | ccgggtaatc | cggcagcctg cgtcgtgacg | 1980 |
| gggctagact | cttgcaatta | tcagtctttc | aacgaggaat | gcctagtagg cgcgagtcat | 2040 |
| cagctcgcgt | cgattacgtc | cctgcccttt | gtacacaccg | cccgtcgctc ctaccgattg | 2100 |
| gatgtgctgg | tgaagcgctc | ggaccggccg | cgtcgcgcgg | ttcgccgcgc ctcgcagccg | 2160 |
| ggaagtccgt | tgaaccctcc | cacctagggg | aaggagaagt | cgtaa | 2205 |